United States Patent [19]

Futamata

[11] Patent Number: 5,291,540
[45] Date of Patent: Mar. 1, 1994

[54] SERVO CONTROLLED ISOCENTER DIAGNOSTIC X-RAY EXAMINATION APPARATUS

[75] Inventor: Shinichiro Futamata, Tochigi, Japan

[73] Assignee: Kabushiki Kaisha Toshiba, Kawasaki, Japan

[21] Appl. No.: 880,221

[22] Filed: May 8, 1992

[30] Foreign Application Priority Data

May 10, 1991 [JP] Japan .................. 3-105461

[51] Int. Cl.⁵ .......................... H05G 1/02; A61B 6/02
[52] U.S. Cl. .................................. 378/197; 378/196; 378/205
[58] Field of Search ............... 378/197, 196, 201, 205, 378/901, 209

[56] References Cited

U.S. PATENT DOCUMENTS

| | | | |
|---|---|---|---|
| 4,769,832 | 9/1988 | Louiday | 378/197 |
| 5,038,371 | 8/1991 | Janssen et al. | 378/197 |
| 5,052,036 | 9/1991 | Grady | 378/197 |
| 5,081,661 | 1/1992 | Larsson | 378/197 |
| 5,155,757 | 10/1992 | Sakaniwa et al. | 378/196 |
| 5,159,622 | 10/1992 | Sakaniwa et al. | 378/196 |

*Primary Examiner*—David P. Porta
*Assistant Examiner*—Kim-Kwok Chu
*Attorney, Agent, or Firm*—Oblon, Spivak, McClelland, Maier & Neustadt

[57] ABSTRACT

An X-ray tube for radiating an X-ray to an object and a detector for detecting the X-ray transmitted through the object are mounted on both ends of a C-shaped arm. The arm is supported by an arm holder such that the C-shaped arm can be slid along an arc portion of the C-shaped arm. The arm holder having a horizontal portion which is supported by a supporting member such that the arm holder rotates around the horizontal portion. The supporting member is suspended from the ceiling via a pole such that the supporting member rotates around the pole and moves in the X and Y directions. When the supporting member is rotated, the supporting member is moved in the X and Y directions in accordance with an angle of rotation such that the C-shaped arm rotates around an isocenter at which a center axis of a circle including the arc portion of the C-shaped arm crosses the horizontal axis of rotation of the arm holder. A control circuit for these operations includes a memory for storing data denoting a predetermined locus of the supporting member in accordance with an angle of rotation, a detector for detecting a locus of the supporting member during rotation, and a servo control loop for controlling movement of the supporting member in accordance with outputs from the memory and the detector.

4 Claims, 7 Drawing Sheets

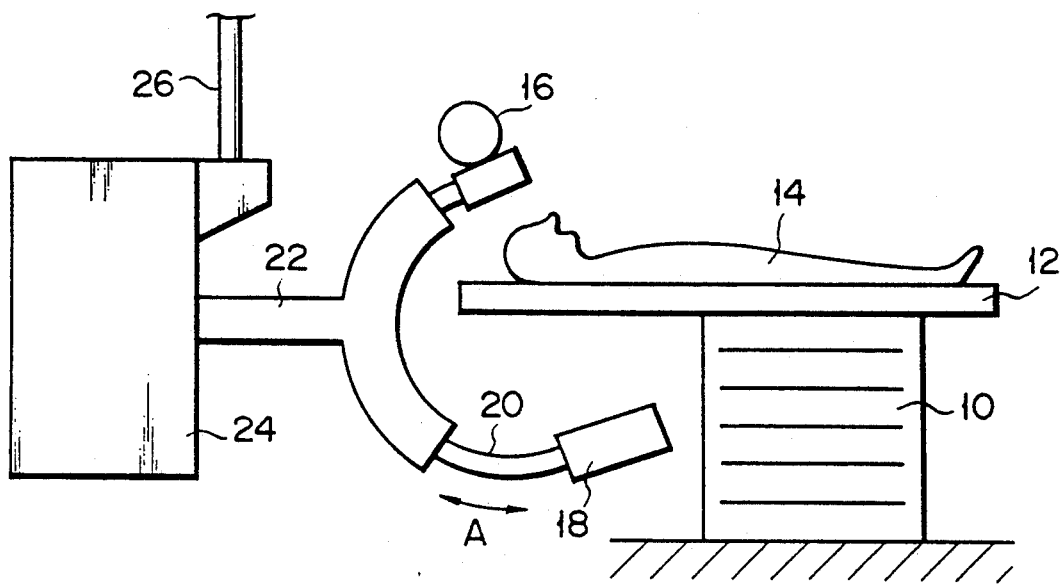
F I G. 2    (PRIOR ART)
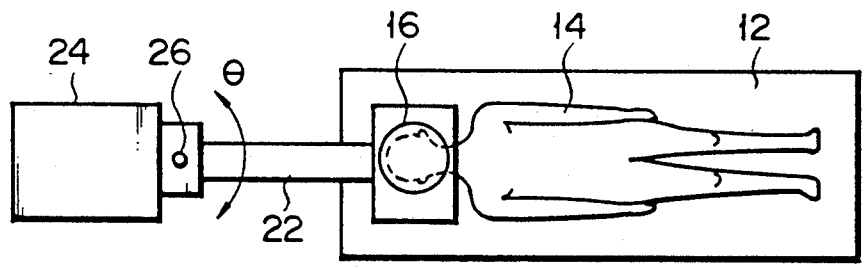
F I G. 3    (PRIOR ART)

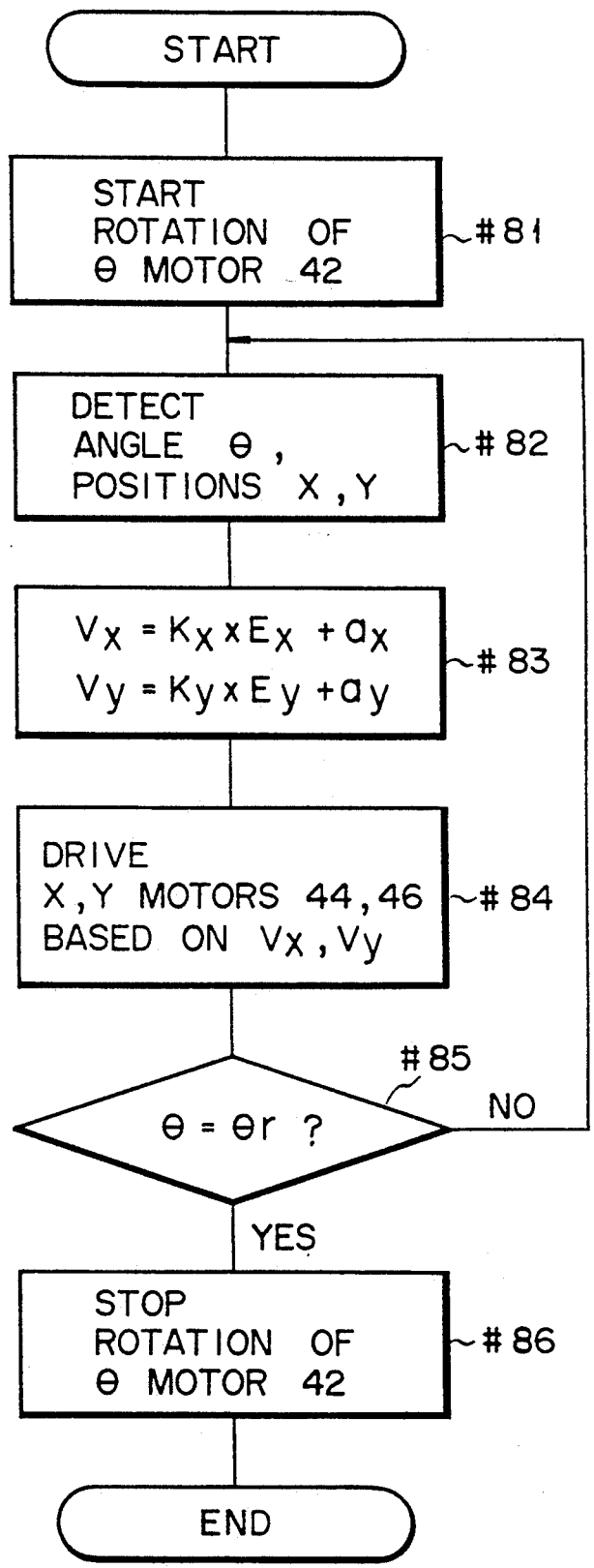
F I G. 8

SERVO CONTROLLED ISOCENTER DIAGNOSTIC X-RAY EXAMINATION APPARATUS

BACKGROUND OF THE INVENTION

1. Field of the Invention

The present invention relates to a diagnostic X-ray apparatus wherein an arm member for supporting an X-ray tube and an image intensifier can be rotated around a vertical axis.

2. Description of the Related Art

A conventional diagnostic X-ray apparatus is shown in FIG. 1. The diagnostic subject of this apparatus is circulatory organs. A patient 14 is laid on a top plate 12 of a bed 10 which is placed on a floor of an examining room or a diagnosis room. An X-ray tube 16 and a detector (including an image intensifier, TV camera, or X-ray film if necessary) 18 are mounted on both ends of a C-shaped arm 20 which is shaped like a semicircular arc so that they are faced to each other with the patient 14 therebetween. An X-ray emitted from the X-ray tube 16 is incident on the detector 18 through the patient 14 and thus an X-ray fluoroscopic image is obtained.

The C-shaped arm 20 is supported by an arm holder 22 which includes an arc portion. The arm holder 22 rotatably slides the C-shaped arm 20 along the arc portion as shown by an arrow A so as to view the patient 14 in an oblique direction other than the front direction, as shown in FIG. 2. The driving source of this slide movement (motor or the like) is provided in the arm holder 22. The axis of this rotational slide is an axis passing through the center of a circle including the arc portion of the arm holder 22.

The arm holder 22 is formed of the arc portion and a horizontal portion which are integrally formed. The horizontal portion supporting the arc portion is horizontally supported by a supporting member 24. The supporting member 24 can rotate the horizontal portion of the arm holder 22 as shown in an arrow B of FIG. 1 and vertically shift the arm holder 22 in the Z direction to adjust the height of the arm holder 22. The driving source of this rotation and movement (motor or the like) is included in the supporting member 24. The axis of the rotation in the direction B, i.e., the horizontal portion of the arm holder 22 crosses the axis of the rotation in the direction A. The crossing point IC is called as an isocenter. If the C-shaped arm 20 is a semicircle arc, the isocenter IC is positioned on the connecting line between the X-ray tube 16 and the detector 18.

The supporting member 24 is suspended from the ceiling of the room via a supporting pole 26. Since the C-shaped arm 20 for supporting the X-ray tube 16 and the detector 18 is considerably heavy, the supporting pole 26 is located on a point which can easily balance the weight of the C-shaped arm 20 and the supporting member 24.

A supporting member 28 for suspending the upper end of the pole 26 is provided in the ceiling. The supporting member 28 can drive or rotate the pole 26 and the C-shaped arm 20 in a θ direction as shown in FIG. 3 and move the pole 26 and the C-shaped arm 20 in a lateral direction X (perpendicular to the sheet plane of FIG. 1) as shown in FIG. 4. The driving source of this rotation and movement (motor or the like) is included in the supporting member 28.

The supporting member 28 is further suspended by a supporting member 30 which is provided in the ceiling. The supporting member 30 can move the C-shaped arm 20 in a longitudinal direction Y (lateral direction in the sheet plane of FIG. 1) as shown in FIG. 5. The driving source of this movement (motor or the like) is included in the supporting member 30.

Though not shown, a Y-guide rail is fixed on the ceiling for guiding the movement of the supporting member 30 in the Y direction, and an X guide rail is fixed on the supporting member 30 for guiding the supporting member 28 in the X direction. As a result, the C-shaped arm 22 can be rotated in the θ direction and moved in the X and Y directions.

If the supporting pole 26 is rotated in the θ direction while the position of the pole 26 is fixed as shown in FIG. 3, the X-ray tube 16 is displaced from the patient 14 and thus it becomes impossible to obtain the fluoroscopic image of the patient 14. Generally, this θ rotation is performed while the arm 20 is rotatably slid in the direction A to obtain the fluoroscopic image in an oblique direction. Alternately, the θ rotation is performed in order to make room for the operator since the C-shaped arm 20 and the supporting member 24 are considerably large. In any case, it is not preferable to displace the X-ray tube 16 from the patient 14.

Therefore, it is proposed that the pole 26 is moved in the X and Y directions in the horizontal plane if the pole 26 is rotated. According to this proposal, the arm 20 is rotated around a vertical axis including the isocenter IC by driving the pole 26 in the θ direction and shifting the pole 26 to a position 26' which is realized by a combination of the X and Y movements, as shown in a broken line of FIG. 6. This type of rotation is called isocentric rotation since the rotation axis passes through the isocenter IC. During the isocentric rotation, the ROI (Region Of Interest) of the patient cannot be outside the field of view of the X-ray tube 16 if the ROI is initially positioned in the field of view.

In the conventional apparatus, the movement of the pole 26 in the X and Y directions in order to perform the isocentric rotation is controlled by an open loop control circuit based on velocity data which is previously calculated in accordance with the angle θ of rotation. That is, the velocity of the motors for moving the supporting members 30 and 28 in the Y and X directions is controlled based on the angle θ of rotation of the pole 26.

However, the conventional open loop control circuit stops the movement of the pole 26 by merely setting the velocity to 0. Therefore, the isocenter may be displaced when the movement of the pole 26 is stopped. If the pole 26 is rotated/stopped many times, the displacement is accumulated which results in a large deviation of the isocenter. In order to prevent this deviation due to the intermittent rotation, it is necessary to confirm the position of the isocenter before the start of rotation and correct the position of the arm if the isocenter is displaced. This is a troublesome work for the operator.

Further, in the conventional open loop control circuit it is assumed that the moving velocity of the pole is a constant velocity. Therefore, it is not possible to perform the isocentric rotation when the initial angle θ of rotation is not 0. If the moving velocity varies due to the change in a load or the amount of movement of the pole 26 exceeds a predetermined level, the isocentric rotation cannot be performed any more.

If the isocentric rotation cannot be performed, the C-shaped arm 20 may be moved unexpectedly. In this case, the operator may be exposed to danger by the supporting member 24 and the arm holder 22.

3

As described above, the conventional apparatus cannot keep the isocenter at a desired position and accurately perform the isocentric rotation.

SUMMARY OF THE INVENTION

Accordingly, it is an object of the present invention to provide a diagnostic X-ray apparatus wherein an arm for supporting an X-ray source and a detector can be rotated in an isocentric manner and keep the isocenter at a desired position.

According to the present invention, there is provided a diagnostic X-ray apparatus comprising an arm member for supporting an X-ray source for radiating an X-ray to an object and a detector for detecting the X-ray transmitted through the object, the X-ray source and the detector facing to each other with the object therebetween; means for supporting said arm member such that said arm member can be rotated around a vertical axis and moved horizontally; and driving means for driving said arm member to rotate around the vertical axis and moving said arm member horizontally in accordance with an angle of rotation of the arm member such that a point at which a line connecting the X-ray source and the detector passes the object does not change during the rotation of said arm member, said driving means comprising means for generating data denoting a predetermined locus of said arm member in accordance with an angle of rotation, means for detecting a locus of said arm member during rotation of said arm member, and servo means for controlling horizontal movement of said arm member in accordance with outputs from said data generating means and detecting means.

According to the present invention, it is possible to keep the isocenter at a desired position and accurately perform the isocentric rotation of the arm, since the position servo control is performed in order to change the position of the arm during the rotation of the arm.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 2 shows a rotational slide of the C-shaped arm along the arc direction of the arm;

FIG. 3 shows a rotation of the C-shaped arm in the $\theta$ direction;

FIG. 8 is a flow chart showing the isocentric rotation of the C-shaped arm according to this embodiment.

DETAILED DESCRIPTION OF THE PREFERRED EMBODIMENTS

Figure 1:
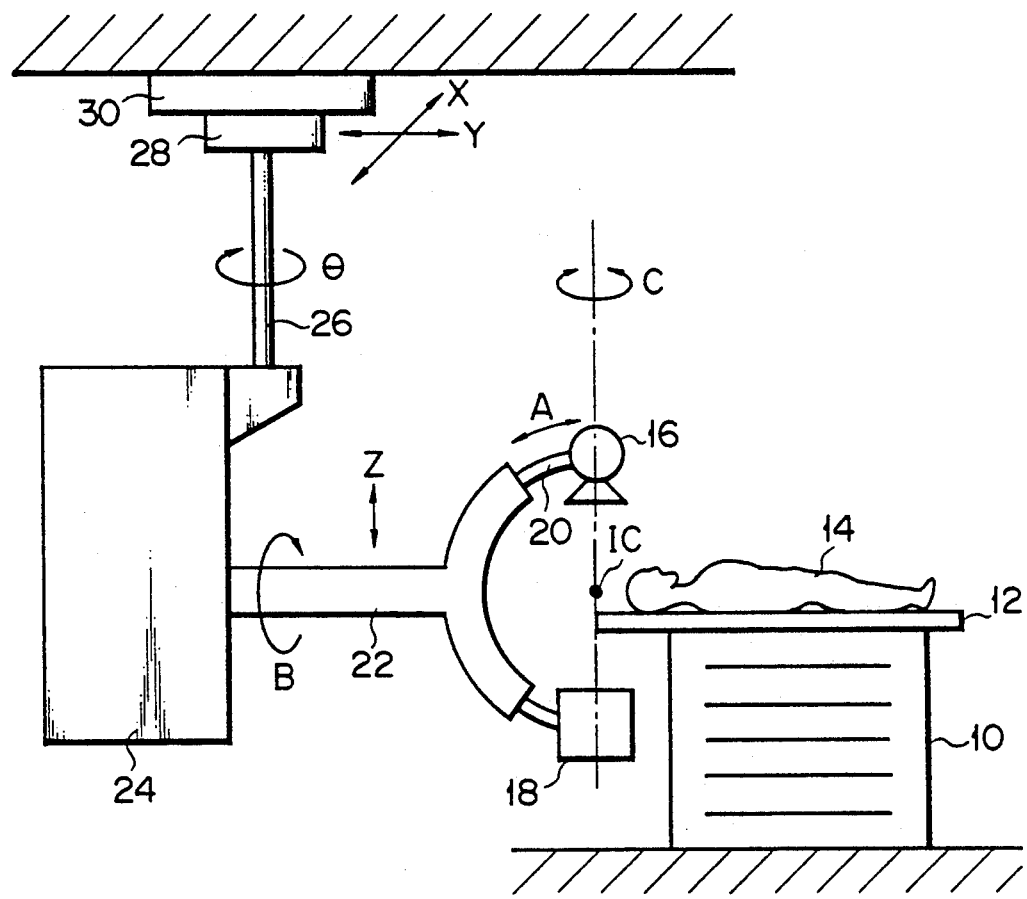
FIG. 1 shows a conventional diagnostic X-ray apparatus for circulatory organs having a C-shaped arm suspended from the ceiling.
Figure 4:
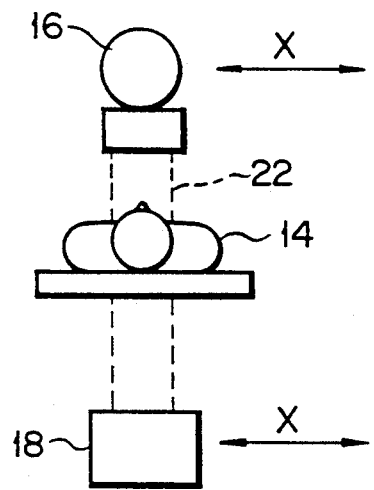
FIG. 4 shows an X directional movement of the C-shaped arm.
Figure 5:
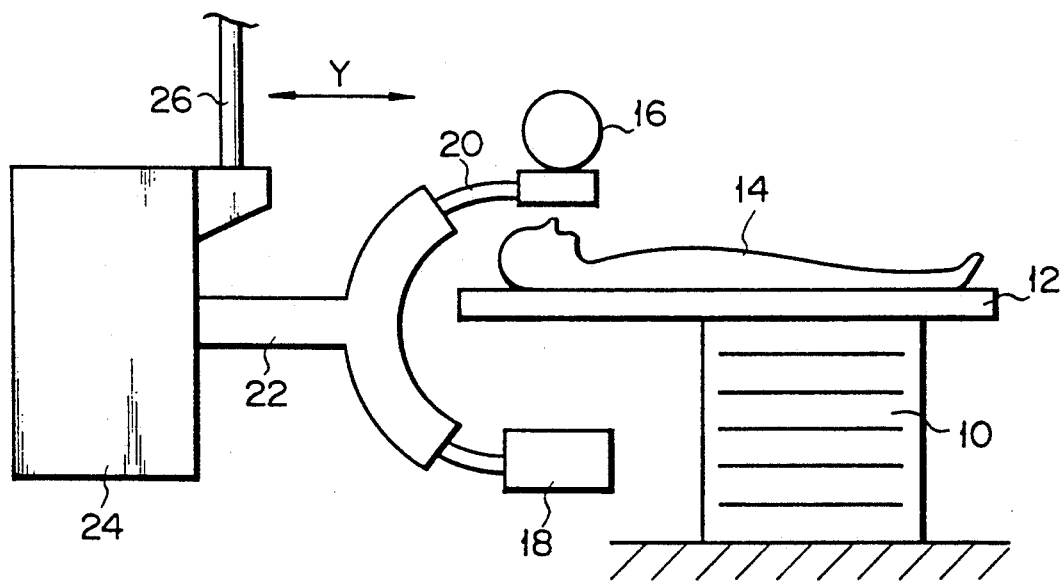
FIG. 5 shows a Y directional movement of the C-shaped arm.

A preferred embodiment of a diagnostic X-ray apparatus according to the present invention will now be described with reference to the accompanying drawings. Since the mechanical construction of the embodiment is similar to that of the conventional apparatus, the detailed description thereof will be omitted and the same reference numerals are used to designate the same parts of the apparatus.

Figure 7:
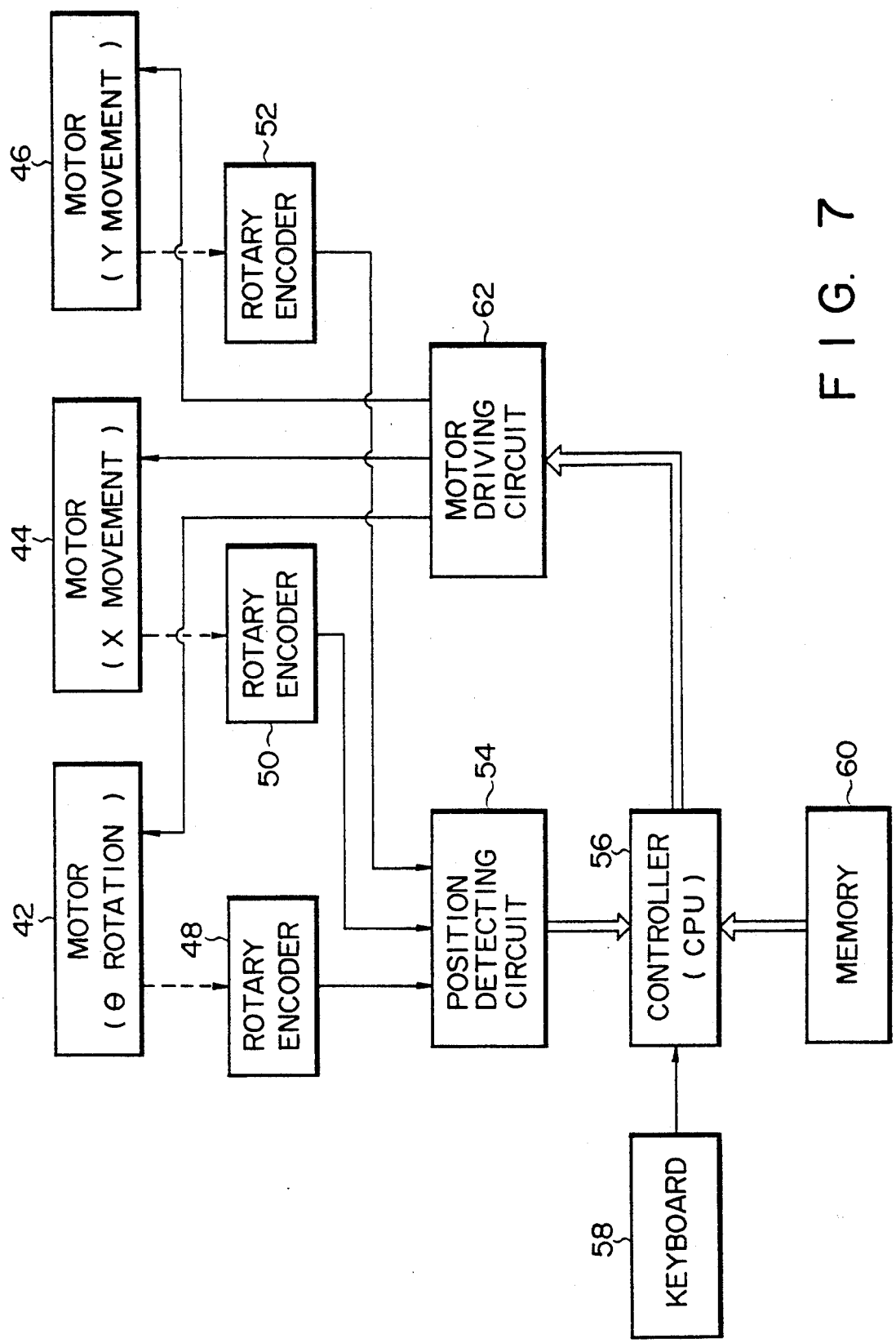
FIG. 7 is a block diagram of an embodiment of a diagnostic X-ray apparatus according to the present invention.

FIG. 7 is a block diagram showing a control circuit for the isocentric rotation. A motor 42 for driving the pole 26 to rotate the C-shaped arm 20 and a motor 44 for moving the pole 26 and the C-shaped arm 20 in the X direction are provided in the supporting member 28. A motor 46 for moving the pole 26 and the C-shaped arm 20 in the Y direction is provided in the supporting member 30. The amount of rotation of the C-shaped arm 20 in the 8 direction and the amounts of movement of the C-shaped arm 20 in the X and Y directions are detected by rotary encoders 48, 50, and 52, respectively. Outputs of the rotary encoders 48, 50, and 52 are supplied to a position detecting circuit 54 formed of a counter or the like.

The position detecting circuit 54 accumulates the outputs from the rotary encoders 48, 50, and 52, thereby detecting the rotation angle $\theta$, the positions X and Y of the pole 26. The detected rotation angle $\theta$ and the positions X and Y of the pole 26 are supplied to a controller 56 formed of a CPU or the like. A keyboard 58 for inputting an instruction of a start of the isocentric rotation and an angle of the isocentric rotation (rotation angle of the pole) and a memory 60 for storing position data denoting the locus of the pole 26 for the isocentric rotation are connected to the controller 56.

Figure 6:
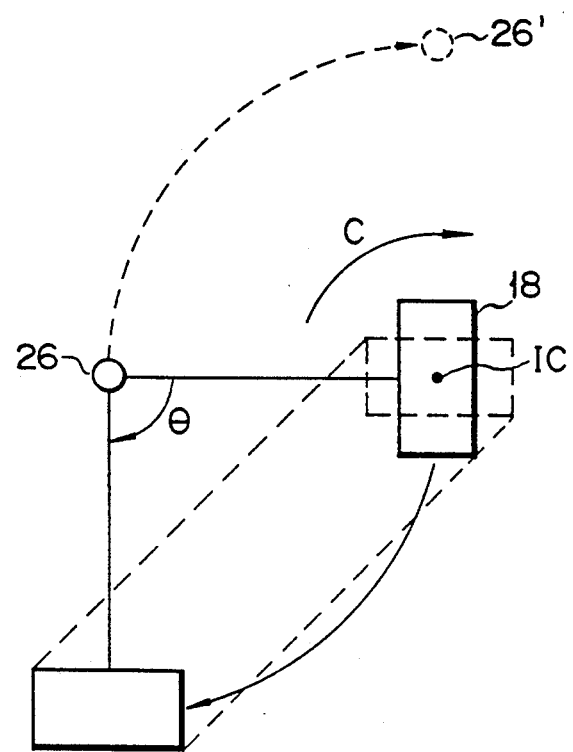
FIG. 6 shows an isocentric rotation of the C-shaped arm around a vertical axis passing through an isocenter.

As shown in FIG. 6, the locus of the pole 26 during the isocentric rotation is determined by a circle having a center which coincides with the isocenter and a radius equal to the distance between the vertical axis passing through the isocenter and the pole 26. The X and Y positions of the pole 26 for every rotation angle $\theta$ can be previously calculated and these data for every rotation angle are stored in the memory 60 as the locus data. Since the length of the arm holder 22 in the Y direction (constant length) is known, it is possible to obtain the position of the isocenter in accordance with the X and Y positions and the angle 8 of the pole 26. It is to be noted that the locus data is represented by a relative distance which is measured from the initial position of the pole at the start of rotation.

The controller 56 supplies velocity data to a motor driving circuit 62 for controlling the X-movement motor 44 and the Y-movement motor 46 based on the outputs from the position detecting circuit 54 and the memory 60. The controller 56 also supplies velocity data to a motor driving circuit 62 for driving the $\theta$-rotation motor 42 in a constant velocity.

The motor driving circuit 62 drives the motors 42, 44, and 46 based on the velocity data supplied from the controller 56.

The isocentric rotation according to the present embodiment will be described with reference to the flow chart shown in FIG. 8. The operator adjusts the X and Y positions and the rotation angle $\theta$ of the pole 26, thereby positioning the ROI of the patient 14 in the field of view of the X-ray tube 16. Then, the operator inputs the instruction to start the isocentric rotation to the controller 56.

At step #81, the controller 56 starts rotation of the motor 42 at a constant velocity. The C-shaped arm 20 rotates around the pole 26 in the $\theta$ direction.

At step #82, the controller 56 detects the current rotation angle $\theta$ and X and Y positions of the pole 26 based on the outputs of the position detecting circuit 54. At step #83, the controller 56 reads out the locus data from the memory 60 in accordance with the detected rotation angle $\theta$. The controller 56 calculates velocity data Vx and Vy based on the difference between the readout locus data and the detected current positions X and Y as follows:

$$Vx = Kx \times Ex + ax$$

$$Vy = Ky \times Ey + ay$$

where Ex and Ey are difference between the detected positions X and Y and the locus data Xo and Yo for the angle $\theta$ read out from the memory 60 (Ex=X−Xo and Ey=Y−Yo), Kx and Ky are gains of a servo loop from the rotary encoders 48, 50, and 52 to the motor driving circuit 62, and ax and ay are offsets of the velocity of the motor below which the motor cannot be responded to the velocity signal. Generally, the motor starts rotation when the velocity signal exceeds a predetermined level.

In the above equations, the offset is simply added to the velocity signal. However, it is possible to add the offset to the velocity signal only when the velocity signal is smaller than a predetermined level and not to add the offset when the velocity signal is not smaller than a predetermined level. Further, it is possible to change the offset in accordance with the angle $\theta$. If the pole is rotated within the range of 0° to 90°, an offset for the angle near 0° and 90° is smaller than that for the other angle. If the offset is small, the velocity of the motor is also low. Therefore, it is easy to stop the pole at $\theta = 0°$ and 90°.

This velocity data is supplied to the motor driving circuit 62. At step #84, the motor driving circuit 62 controls the driving velocities of the X-movement and Y-movement motors 44 and 46 based on the above equations. As a result, the motors 44 and 46 are controlled such that the positions X and Y of the pole 26 exactly trace the predetermined locus which is necessary for the isocentric rotation.

At step #85, it is determined whether or not the rotation angle $\theta$ of the C-shaped arm 20 reaches the predetermined angle $\theta r$ which is input by means of the keyboard 58. If the C-shaped arm 20 is not rotated up to the predetermined angle $\theta r$, the flow returns to the step #82 and the above positional servo control is repeated. If the C-shaped arm 20 is rotated over the predetermined angle $\theta r$, the rotation of the $\theta$ motor 42 is stopped at step #86 and the operation ends.

Figure 9:
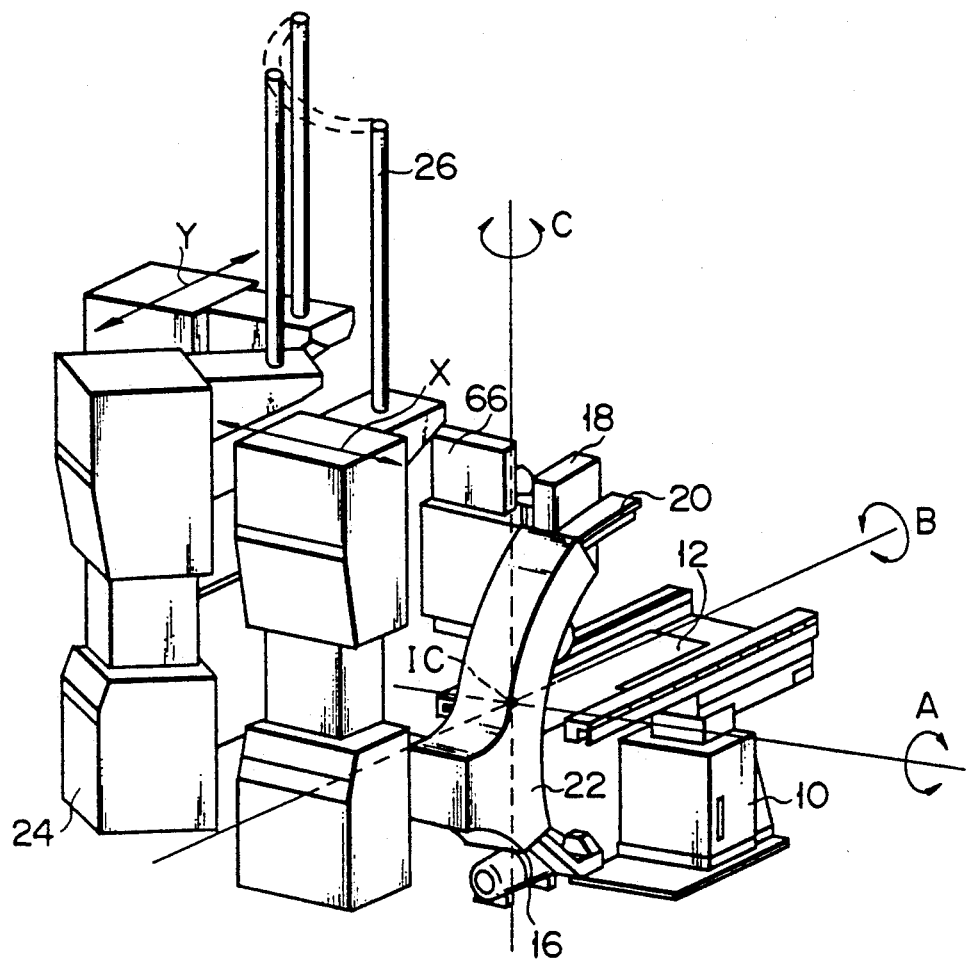
FIG. 9 shows the isocentric rotational of the C-shaped arm according to this embodiment.

FIG. 9 shows the movement ($\theta$ rotation and X- and Y-movements) of the pole 26 and the C-shaped arm 20 during the isocentric rotation. In FIG. 9, the arm holder 22 is rotated around the horizontal portion to position the X-ray tube 16 under the patient and the detector 18 over the patient. Thus, the positional relationship between the X-ray tube 16 and the detector 18 is reverse to that shown in FIG. 1. Further, a film changer 66 is provided near the detector 18 to photograph the fluoroscopic image using the X-ray film. FIG. 9 shows the case in which the C-shaped arm 20 is not rotatably slid in the direction A (the line connecting the X-ray tube 16 and the detector 18 is vertical) and the C-shaped arm 20 has a semicircular arc. Therefore, the axis of the isocentric rotation coincides with the line connecting the X-ray tube 16 and the detector 18. However, if the C-shaped arm 20 is rotatably slid in the direction A, the axis of the isocentric rotation is a vertical line passing through the point at which the axis of the rotation in the direction A crosses the axis of the rotation in the direction B.

As described, according to the present embodiment, the position servo control is performed in order to change the position of the C-shaped arm during the rotation of the C-shaped arm 20 around the pole 26. Therefore, it is possible to keep the isocenter at a desired position and accurately perform the isocentric rotation of the C-shaped arm 20. Since the servo control continues until the angle of the isocentric rotation reaches the desired angle, it is never displace the isocenter when the movement of the pole 26 is stopped Thus, it is not necessary to confirm the position of the isocenter before the start of rotation and correct the position of the arm even in the case of the intermittent rotation.

Since the locus of the pole for the isocentric rotation is determined, it is possible to perform the isocentric rotation even if the initial angle $\theta$ of rotation is other than 0°. If the moving velocity varies due to the change in a load or the amount of movement of the pole 26 exceeds a predetermined level, the movement of the pole 26 is rapidly returned to the predetermined movement.

Moreover, the operator can concentrate his or her attention on a diagnosis operation thereby improving the diagnosis since the isocentric rotation is assured.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents. For example, the present invention can be applied to any diagnostic X-ray apparatus other than the apparatus for circulatory organs wherein the arm for supporting the X-ray tube and the detector is driven to perform the isocentric rotation. The shape of the arm is not limited to the C-shaped. It is possible to suspend the bed from the ceiling and support the arm by a supporting member which is placed on the floor and can be moved in the X and Y directions.

What is claimed is:

1. A diagnostic X-ray apparatus, comprising:
   a C-shaped arm member having an arc portion and for supporting an X-ray source for radiating an X-ray to an object and a detector for detecting the X-ray transmitted through the object, the X-ray source and the detector mounted at ends of the C-shaped arm member so as to face each other with the object therebetween;
   an arm holder for supporting said C-shaped arm member such that said arm member can be slid along the arc portion and rotated around a horizontal axis contained in a plane of said arm member so as to change a directional relationship between the X-ray tube and the object, the X-ray apparatus having an isocenter at an intersection of a line connecting the X-ray source and the detector, and said horizontal axis;

a vertical suspension pole, offset from said isocenter such that an axis of said suspension pole is without an intersection with said isocenter, for suspending said arm holder from a ceiling;

means for moving said suspension pole within a ceiling plane in an X direction;

means for moving said suspension pole within a ceiling plane in a Y direction, parallel to said X direction;

rotating means for rotating said suspension pole and thereby rotating said arm holder and said C-shaped arm member;

means for detecting an angle $\theta$ of the suspension pole;

means for setting a velocity of the suspension pole in the X and Y directions such that as the angle $\theta$ of the suspension pole changes, the isocenter remains in substantially a same position, the means for setting a velocity including:

means for setting the velocity in the X direction such that:

$$Velocity_x = K_x * (X - X_o)$$

and the velocity in the Y direction is set such that:

$$Velocity_y = K_y * (Y - Y_o)$$

where $K_x$ is a constant, X is a detected position in the X direction and Xo is predetermined locus data, and $K_y$ is a constant, Y is a detected position in the Y direction and Yo is a predetermined locus position.

2. An apparatus according to claim 1 wherein the velocities in the X and Y direction are determined using a velocity offset.

3. An apparatus according to claim 2, where $K_x$ and $K_y$ are gains of a servo loop.

4. An apparatus according to claim 1, where $K_x$ and $K_y$ are gains of a servo loop.

* * * * *